(12) United States Patent
Schmitz et al.

(10) Patent No.: US 11,609,199 B2
(45) Date of Patent: Mar. 21, 2023

(54) NANOSTRUCTURED TITANIUM MULTILAYER ELECTRODE (71) Applicant: Fraunhofer-Gesellschaft zur Förderung der angewandten Forschung e.V., Munich (DE)

(72) Inventors: Tobias Schmitz, Würzburg (DE); Mattias Schweinlin, Würzburg (DE); Florian Gröber-Becker, Würzburg (DE); Jan Hansmann, Würzburg (DE); Marco Metzger, Würzburg (DE); Thomas Schwarz, Würzburg (DE); Heike Walles, Würzburg (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 277 days.

(21) Appl. No.: 16/759,965

(22) PCT Filed: Oct. 22, 2018

(86) PCT No.: PCT/EP2018/078934
§ 371 (c)(1),
(2) Date: Apr. 28, 2020

(87) PCT Pub. No.: WO2019/086290
PCT Pub. Date: May 9, 2019

(65) Prior Publication Data
US 2020/0340095 A1    Oct. 29, 2020

(30) Foreign Application Priority Data
Oct. 30, 2017  (DE) .............. 10 2017 219 425.1

(51) Int. Cl.
*G01N 27/12*    (2006.01)
*C23C 14/00*    (2006.01)
(Continued)

(52) U.S. Cl.
CPC .......... *G01N 27/12* (2013.01); *C12M 1/3407* (2013.01); *C23C 14/0084* (2013.01);
(Continued)

(58) Field of Classification Search
CPC .............. C12M 1/3407; C23C 14/0036; C23C 14/0084; C23C 14/0641; C23C 14/205; C23C 28/42; G01N 27/12
See application file for complete search history.

(56) References Cited

U.S. PATENT DOCUMENTS 4,603,704 A    8/1986   Mund et al.
5,561,326 A *  10/1996  Ito .................... H01L 21/2855
                                                     257/E21.585
(Continued)

FOREIGN PATENT DOCUMENTS

DE    3300668    7/1984
EP    2876435    5/2015

OTHER PUBLICATIONS

Angstmann et al. Monitoring human mesenchymal stromal cell differentiation by electrochemical impedance sensing; Cryotherapy, 2011; 13, pp. 1074-1089.*

(Continued)

*Primary Examiner* — Benjamin R Whatley
(74) *Attorney, Agent, or Firm* — Sheppard Mullin Richter & Hampton LLP (57) ABSTRACT

A multilayer electrode on a substrate (10) comprising titanium (20) and titanium-rich titanium nitride (30) and titanium-poor titanium nitride (40), particularly suitable for the application to thermoplastic substrates, in particular for the purpose of the impedance measurement in aqueous biological media, and method for the production thereof.

14 Claims, 8 Drawing Sheets

(51) Int. Cl.
*C23C 14/06* (2006.01)
*C23C 14/20* (2006.01)
*C12M 1/34* (2006.01)

(52) U.S. Cl.
CPC ........ *C23C 14/0641* (2013.01); *C23C 14/205* (2013.01); *B01L 2300/0645* (2013.01)

(56) References Cited

U.S. PATENT DOCUMENTS

| | | | | |
|---|---|---|---|---|
| 5,985,759 | A * | 11/1999 | Kim | C23C 14/32 438/653 |
| 6,045,666 | A * | 4/2000 | Satitpunwaycha | C23C 14/32 204/192.15 |
| 10,134,629 | B1 * | 11/2018 | Hung | H01L 23/53266 |
| 2002/0089027 | A1 * | 7/2002 | Xu | H01L 23/53238 257/E21.585 |
| 2009/0246243 | A1 | 10/2009 | Martinu et al. | |
| 2010/0032842 | A1 | 2/2010 | Herdt et al. | |
| 2011/0087615 | A1 | 4/2011 | Richardson-Burns et al. | |

OTHER PUBLICATIONS

Aryan et al., "In Vitro Study of Titanium Nitride Electrodes for Neural Stimulation", 33rd Annual International Conference of the IEEE EMBS, 2011, 3 pages.

Norlin et al., "Investigation of Interfacial Capacitance of Pt, Ti and TiN Coated Electrodes by Electrochemical Impedance Spectroscopy", Biomolecular Engineering, 19, (2002), pp. 67-71.

International Search Report and Written Opinion for PCT/EP2018/078934 dated Feb. 15, 2019, 12 pages.

* cited by examiner

NANOSTRUCTURED TITANIUM MULTILAYER ELECTRODE

CROSS-REFERENCE TO RELATED APPLICATIONS

This application is a U.S. National Stage Application under 35 U.S.C. 371 of International Application No. PCT/EP2018/078934, filed Oct. 22, 2018, which claims priority to German Patent Application 10 2017 219 425.1, filed Oct. 30, 2017. The contents of each of the aforementioned are hereby incorporated by reference in their entirety into the present disclosure.

The present invention relates to a multilayer electrode of titanium and titanium nitride, suitable for the application to thermoplastic substrates, in particular for the purpose of impedance measurement in aqueous biological media, and methods for the production thereof.

The invention relates to the technical field of the determination of electrical parameters of biological cells and tissues in liquid biological media, in particular means for the electrical impedance measurement of the complex electrical resistance, for example of the transepithelial resistance (TEER) of cultivated cells or single- or multilayer tissues in cell culture chambers or reactor modules.

In vitro tissues or organ models can be produced by means of cultivated biological cells, on which for example the effect of substances, in particular of pharmaceutical active agents or ingredients of cosmetics or food, are examined with regard to their biocompatibility. In particular the conducting of usual animal tests can thus be avoided. The impedance spectroscopy is a method for the continuous and thus destruction-free examination of physiological parameters of in vitro models of this type. A conclusion can be drawn to the integrity of the tissues, for example to the layering and intactness, but also to physiological processes on or in the tissues, for example transport processes or channel openings by means of the complex technical resistances of the examined in vitro tissues. In vitro tissues of this type are advantageously carried out in parallel approaches in multiple-use culture plates (multi-well plates). Ideally, these parallel approaches are processed in cultivation machines in an automated manner The used cell culture plates are thus generally disposable vessels. However, this type of the parallel approaches opposes an increased use of the impedance spectroscopy, because measuring electrodes, which are set up on the basis of expensive precious metals, such as gold or platinum, are currently carried out for the impedance spectroscopy. They had been required until now, because they have a sufficient chemical stability and guarantee a long and reliable connection as electrode with constant electrical properties. Due to the high costs, materials of this type are only partially suitable for automatable in vitro systems.

It has been shown at the same time that in particular the precious metal-based electrodes or electrode materials derived therefrom have unfavorable impedance properties, such as high resistance and high phase shift, in particular in the lower frequency range.

Due to the high acquisition costs of these expensive electrode materials, impedance spectroscopy systems based thereon are designed for multiple use. After each use, they have to be thoroughly cleaned and sterilized, in order to keep the risk of contamination low. This is not practicable in automatable in vitro systems.

Up to now, impedance measurements of this type have thus only been used serially or in parallel approaches in small numbers in automatable in vitro systems, which reduces the validity of the impedance measurement on the one hand.

On the one hand, the currently available measuring chambers are thus associated with high acquisition and operating costs, the electrode materials used in this available measuring chambers simultaneously have a comparatively low sensitivity. The necessity of the sterilizability for the recurring use also requires that the measuring chambers are made of comparatively expensive polymers, which need to be autoclavable.

The technical problem on which the present invention is based was thus to provide a cost-efficient electrode, suitable for the impedance measurement in biological media, which overcomes the afore-described disadvantages and which can in particular be produced cost-efficiently, has improved electrical properties for the impedance measurement, and/or can be applied to conventional standard cell culture plates of low-melting thermoplastics or other means for the cell and tissue culture.

The technical problem is solved completely by the provision of a novel titanium-based electrode, which is multi-layered and in particular has two titanium nitride layers located one on top of the other, wherein a titanium-rich titanium nitride intermediate layer with stoichiometrically increased titanium content and a titanium-poorer titanium nitride cover layer with stoichiometrically reduced titanium content are formed on a titanium carrier layer.

A first subject matter of the present invention is thus a titanium electrode, which is particularly suitable for the impedance measurement in aqueous biological media and which can in particular be readily applied to a thermoplastic polymeric substrate, wherein the titanium electrode on a substrate is first formed a titanium carrier layer of elemental titanium, a titanium-rich titanium nitride intermediate layer, which rests on the titanium carrier layer, and a titanium-poorer titanium nitride cover layer, which rests on the titanium-rich titanium nitride intermediate layer.

Specifically, this is:
- a (lower) Ti-carrier layer, consisting of elemental titanium (Ti),
- at least one titanium-rich titanium nitride ($TiN_x$) intermediate layer, containing or consisting completely of $TiN_x$, wherein x is smaller than 1 or x equals 1, which rests, in particular immediately and directly, on the Ti carrier layer, and
- a titanium-poor titanium nitride ($TiN_y$) cover layer, containing or consisting completely of $TiN_y$, wherein y is greater than 1, which rests, in particular immediately and directly on the afore-mentioned titanium-rich $TiN_x$ intermediate layer.

Exactly one titanium-rich titanium nitride ($TiN_x$) intermediate layer is preferably provided in the above-mentioned layer sequence of the titanium electrode according to the invention. In preferred design, the sole $TiN_x$ intermediate layer consists of $TiN_x$, with x from 0.3 to 1.0, particularly preferred from 0.6 to 0.9.

In an alternative preferred version, more than one titanium-rich titanium nitride ($TiN_x$) intermediate layer are provided in this layer sequence, wherein a first lower titanium-rich intermediate layer has a higher titanium content than the respective further titanium-rich intermediate layer resting thereon. The lowermost TiN layer of the electrode is the titanium-richest one. The TiN layers following in the layer sequence are each less titanium-rich or titanium-poorer, respectively. A first, titanium-richest $TiN_x$ intermediate layer thereby preferably has x from 0.3 to 0.6, particularly preferably from 0.3 to 0.5, a further titanium-rich TiN$_x$ intermediate layer resting directly thereon thereby preferably has x from 0.5 to 1.0, particularly preferably from 0.6 to 0.9, wherein the further intermediate layer has a lower titanium content than the intermediate layer located immediately therebelow.

In preferred embodiment, the TiN$_y$ cover layer consists of TiN$_y$, with y from 1.1 to 1.5, particularly preferred from 1.2 to 1.4.

The inventors found surprising that such a multilayer electrode, which by means of physical vapor deposition, specifically by reactive cathode sputtering (reactive sputtering), can also readily be applied to low-melting thermoplastic substrates, preferably in a single step. Comparatively thin electrode layers are thus preferred. It has been shown that thin electrode layers can be produced without or without noteworthy thermal stress to the substrate material. Above all, the focus here is on avoiding the softening of the polymeric substrate, in particular in the case of low-melting plastics. An exceeding of the glass transition temperature for amorphous thermoplastics or of the melting temperature of partially crystalline thermoplastics, respectively, is to be prevented or is to at least be limited to the location of the deposition of the electrode layers.

The total thickness of the multiplayer electrode is preferably 3000 nm or less, in particular less than 2000 nm. The thickness of the TiN layers of the multiplayer electrode is preferably 3000 nm or less or 2000 nm or less, but in particular less than 1000 nm. At least the at least one TiN$_x$ intermediate layer, however, thereby has a thickness of 100 to 500 nm, preferably of 150 to 250 nm. In the case of an electrode comprising more than one intermediate layer, each of the intermediate layers can preferably have a thickness of 100 to 500 nm, particularly preferably of 150 to 250 nm. The TiN$_y$ cover layer preferably has a thickness of 500 to 5000 nm, particularly preferably of 300 to 2000 nm.

The inventive three-layer electrode surprisingly has excellent electrical properties even in the case of thin layers, in particular with regard to the impedance behavior, especially in the frequency range is essential for the impedance-spectroscopic measurement of biological material. According to recognizes standards, the TEER measurement takes place at approximately 12.5 Hz. The at least three-layer titanium electrode according to the invention is particularly well suited for the impedance-spectroscopic measurement of biological cells and tissues in aqueous biological media, in particular in commonly known cell culture media. In contrast to the precious metal electrodes, which, as is well-known, are used for this purpose, which are based on gold and/or platinum, the titanium electrode according to the invention has a significantly improved sensitivity, in particular in the low frequency range, which is particularly important for the characterization of in vitro tissues. In contrast to other thin titanium electrodes, which have a Ti base layer and only a single titanium nitride deposited thereon, the titanium electrode according to the invention is also far superior electrically in particular in this low frequency range. It has been shown that the titanium-rich TiN$_x$ intermediate layer has a higher density and thus has a higher conductivity and that the titanium-poorer TiN$_y$ cover layer has a lower density and has particularly good impedance properties in particular due to its more open structure; the titanium-poorer TiN$_y$ cover layer has a particularly low impedance. The surprisingly good electrical properties can be explained in particular by the interaction of more conductive intermediate layer and low-impedance cover layer.

It has been shown that TiN$_y$ cover layer and TiN$_x$ intermediate layer are present best at a certain thickness ratio to one another. The thickness of the TiN$_y$ cover layer, particularly in the case of a three-layer titanium electrode comprising a cover layer and comprising a single intermediate layer, is preferably 1 to 10 times, in particular 1.5 to 4 times the thickness of the TiN$_x$ intermediate layer. Particularly, it is thereby preferably provided that the three layers, which form the electrode, have a thickness ratio of 1-5/1/1-10 to one another, preferably 1-5/1/1.5-4 to one another, referred to Ti carrier layer/TiN$_x$ intermediate layer/TiN$_y$ cover layer.

In particular in the case of a titanium electrode comprising more than three layers, that is, comprising a cover layer and comprising more than one intermediate layer, the thickness of the TiN$_y$ cover layer is preferably 0.5 to 10 times, particularly preferably 0.5 to 4 times, the thickness of the TiN$_x$ intermediate layers. In particular, it is thereby preferably provided that the layers, which form the electrode, have a thickness ratio of 1-5/1/0.5-10, preferably 1-5/1/0.5-4 to one another, referred to the Ti carrier layer/totality of the TiN$_x$ intermediate layers,/TiN$_y$ cover layer.

It is shown at the same time that the inventive titanium electrode according to the invention has a high chemical stability and can thus be readily used for the continuous and longer-term impedance measurement during the cultivation or determination of active agent effects in reactors for cells or in vitro tissues Due to the low process temperature during the creation of the titanium electrode according to the invention, also commercially available standardized single-use cell culture plates, which are routinely made of low-melting thermoplastics, for example by injection molding or comparable methods, can in particular also be coated directly, so that titanium electrodes according to the invention can advantageously be applied directly to single-use cell culture plates or similar systems for storing or for guiding aqueous cell culture media. In this way, single-use measuring chambers comprising titanium electrodes can be provided in a cost-efficient manner and in large numbers, which makes it possible to carry out parallel impedance measurements in all cell culture vessels simultaneously and possibly continuously for the entire duration of the cultivation of the tissues and/or of the substance effect in the automatable in vitro cultivation. There is no longer the necessity for the use of reusable systems and the complex cleaning thereof.

A further subject matter of the invention is a novel method for producing a titanium electrode according to the invention, in particular for applying the titanium electrode to a cell culture plate or generally a measuring module of a polymeric thermally sensitive material, which serves as substrate for the titanium electrode.

The method according to the invention is based on the physical vapor deposition in the form of the reactive cathode sputtering and takes place in the presence of a process gas. Depending on whether a pure titanium layer or a titanium nitride layer is to be deposited, the process gas consists of an inert gas, preferably argon, or of a mixture of the inert gas, preferably argon, and nitrogen gas, respectively.

According to the invention, the method includes at least the following steps: step (b): titanium is sputtered onto a substrate in the presence of a process gas, containing argon and nitrogen, namely at an increased generator power, in order to deposit a first layer consisting of titanium-rich titanium nitride on a titanium carrier layer. Thereafter, the generator power is reduced immediately in step (c) and titanium is sputtered onto the substrate at reduced generator power in step (d), in order to deposit a second layer, consisting of titanium-poor titanium nitride, on the formed titanium-rich titanium nitride layer.

In a variation of the invention, a titanium electrode is formed, which has more than one titanium-rich intermediate layer in its layer sequence. For this purpose, it is provided in particular that steps b) and c) are passed through several times, in order to deposit at least one further titanium nitride intermediate layer, consisting of the titanium-rich TiNx, on a first titanium nitride intermediate layer, wherein the further titanium nitride intermediate layer is titanium-poorer than the respective titanium-richer titanium nitride intermediate layer deposited beforehand. For this purpose, it is provided in particular according to the invention that the generator power is in each case reduced as compared to the previous pass-through in the respective steps c) for each pass-through of steps b) and c), in order to form the titanium-poorer further titanium nitride intermediate layer on one of the respective titanium-richer titanium nitride intermediate layer (30), which had in each case been deposited beforehand.

According to the invention, it is provided in particular that steps b) to d) are carried out immediately consecutively in one pass-through, in order to form the two titanium nitride layers. It is preferably provided that the increased generator power in step b) is 1.2 times to 2.4 times as high as the generator power in step d). To form an electrode comprising several intermediate layers, it is provided, for example, that the first intermediate layer in step b) is deposited at a 2.4 times increased generator power, that, in order to create a particularly titanium-rich titanium nitride intermediate layer, the generator power in step c) is reduced immediately, so that in step b) of the further pass-through a second (or further) intermediate layer is deposited with an only 1.2 times increased generator power, in order to create a less titanium-rich further titanium nitride intermediate layer, and the generator power in step c) of the further pass-through is subsequently reduced immediately again, so as to ultimately create the titanium-poor titanium nitride cover layer in step d) with non-increased generator power.

It is preferably provided that the composition of the process gas (argon/nitrogen) is kept constant, in particular based on the nitrogen partial pressure, during steps b) to d).

Step b) is preferably preceded by step a), in which a titanium carrier layer is deposited on a substrate, preferably on a polymeric substrate, particularly preferably of a thermoplastic substrate. Step a) preferably takes place in a PVD process of the reactive cathode sputtering by sputtering titanium onto the polymeric substrate in the presence of a process gas, consisting of inert gas, preferably argon.

The method according to the invention is thus particularly characterized in that the two titanium nitride layers, the titanium content of which differs, are deposited immediately consecutively, whereby the stoichiometric ratio in the titanium nitride is created by immediately changing the generator power in the cathode sputtering. An increased generator power thereby creates a titanium-rich titanium nitride layer, a generator power, which is reduced in comparison, thereby creates a titanium-poorer titanium nitride layer. Due to this immediate switch-over of the generator power during the depositing process, it is advantageously possible to reduce the process duration of the layer deposition on the substrate as a whole, which prevents that the substrate heats up excessively. This advantageously allows for the use of low-melting thermoplastics as substrate, whereby it is made possible to provide normal standard cell culture plates or other polymeric laboratory vessels for storing and guiding liquid biological media with a titanium electrode, which is particularly suitable for the impedance measurement in these biological media. High-quality electrodes for the impedance measurement can be formed in this way at conventional cell culture vessels and similar laboratory equipment in a simple and cost-efficient manner The method according to the invention is thus in particular designed such that the substrate (10) consists of a low-melting thermoplastic or contains the latter.

The polymeric substrate is preferably selected from the group of the, in particular low-melting, thermoplastics, preferably consisting of: polystyrene (PS), polyamide (PA), in particular PA6, PA6.6; acrylonitrile butadiene styrene (ABS); polylactic acid (PLA); polycarbonate (PC); polyethylene terephthalate (PET), polyethylene (PE), polycaprolactone (PCT); polypropylene (PP); polyetheretherketone (PEEK), polyimide (PI), polyurethane (PU), and polyvinylchloride (PVC) as well as combinations, mixtures, and co-polymers thereof.

Standard cell culture vessels, such as multi-well plates, but also membrane reactors, hollow fiber modules, but also other laboratory equipment for storage and guidance of liquid biological media, such as, for example, hose connecting pieces, fittings, hose pieces, etc., can accordingly be provided immediately and directly with this titanium electrode.

In one variation, however, the invention does not rule out that other, thermally stable materials can also be used as substrates. The technical advantage attained with the titanium electrode according to the invention does not only extend to the improved applicability onto polymeric materials. The excellent electrical properties of the titanium electrode according to the invention, in particular at small layer thicknesses, are also attained when thermally stable materials are used. They are preferably selected from the group of the metals and metal oxides, in particular consisting of: titanium, stainless steel, magnesium, aluminium oxides, titanium oxide, and combinations thereof, namely preferably in massive form or as in particular open-pored sinter structure. Examples are substrates of sintered ceramics.

A method for producing a measuring module, in which the liquid medium can be guided, for the impedance measurement in aqueous biological media, including the steps: providing the module as substrate of the electrode and depositing the titanium electrode on the substrate by means of the method according to the invention described herein, is thus also subject matter of the invention.

A (general) measuring module, in which the liquid medium can be guided, for the impedance measurement in aqueous biological media, containing or consisting of a substrate and of at least one multilayer titanium electrode, which is preferably deposited immediately on this substrate, as it is described herein, is thus also subject-matter of the invention.

A measuring module of this type, on which the titanium electrode according to the invention can be formed, is preferably selected from: cell culture vessels, multi-well plates, membrane reactors, hollow fiber modules, hose connecting pieces.

A particularly preferred embodiment is a multi-well plate (microtiter plate), which is known per se, which carries at least one titanium electrode according to the invention at least in the bottom area of one, in particular of each, well. Said titanium electrode is preferably deposited directly on the bottom portion of the polymeric multi-well plate. Electroconductive structures or conductor tracks for contacting the electrode are preferably formed on the well. They end, for example, on the upper side of the well or preferably run towards a common integral contacting surface on the edge of the multi-well plate, in order to provide for a preferably multi-channel contacting of all electrodes in all wells. This is practicable in particular for an automated processing, that is, automated handling of the culture plates. The conductor tracks for contacting the electrode are preferably also formed in the manner and dimensioning of the electrode. Particularly preferred, electrode and conductor track are applied to the substrate in one processing step, that is, in particular by means of the coating method described herein. It is accordingly preferred that the entire current conduction leads over the thin cross-section of the layer system, whereby the resistance is comparatively low here, as in the case of a layer, which would be applied to a conductive full material.

Another preferred design is a hose connecting piece (fitting) or intermediate piece on or for use on a reactor module. This connecting piece advantageously serves for the pass-through of biological media from and out of a reactor module. The connecting piece is formed as measuring module and has, for this purpose, the titanium electrode according to the invention at least on the side facing the biological medium (lumen). Said titanium electrode is preferably deposited at least there directly on the polymeric material of the connecting piece itself. Conductive structures, preferably the titanium electrode coating itself, lead from the media contact side (media-guiding lumen) to the outside, where means, which are known per se, for the electrical contacting can engage. In a variation, which can be constructed easily, the connecting pieces are standard laboratory Luer-Lock hose connecting pieces for connecting media-guiding hoses to corresponding Luer-Lock compression fittings. These hose connecting pieces of polymeric material itself are provided with the titanium electrode coating.

In another embodiment according to the invention of the connecting piece, that is, in particular fitting or also hose, a separate carrier structure is inserted therein, on which the titanium electrode according to the invention is deposited. This carrier structure is preferably a net or mesh of metallic material, in particular stainless steel, or particularly preferably of an afore-mentioned polymeric material, in particular nylon (PA6, PA6.6). In the case of a variation thereof, which can be constructed easily, the net-shaped or mesh-shaped titanium electrode of the invention is inserted directly into a polymeric hose for liquid media, in particular a standard laboratory silicon hose.

A variant of this is a hollow membrane reactor, which has the titanium electrode according to the invention in the area of the hose connections, in particular at the inlets and outlets. According to the invention, the titanium electrode coating is preferably formed on the inner side of the hose connections, where it is in contact with the liquid media, such as dialysates. Alternatively, at least a part of the reactor housing, in particular in the area of the end caps of a hollow membrane reactor, is provided with a titanium electrode coating according to the invention.

The invention will be described by means of the following figures and examples, which should not be understood as being limiting.

FIGS. 1A and 1B show a schematic view of a measuring module according to the invention in the form of a connecting piece (150). The illustration is not scaled. A multilayer titanium electrode (50) according to the invention is formed on a carrier, which is tubular on principle, of polymer as substrate (10), at least on a portion. As shown in the sectional view in FIG. 1A (sectional plane "A" as in FIG. 1B), said titanium electrode in each case has a three-layer setup: a titanium layer (20) is deposited directly on the substrate (10), on it a titanium-rich TiN intermediate layer (30), on it a titanium-poor TiN cover layer (40). The diagonal view in FIG. 1B shows the connecting piece (150) for guiding liquid medium (arrow) with the titanium electrode (50), which extends into the media-guiding interior (lumen) of the tubular carrier (10) and, for the purpose of the electrical contacting, also towards the outer side, in the illustrated preferred variation.

FIG. 2 additionally shows a cover or stamp (110), which can preferably be used. The latter has electrode carriers (112), which, when in use, can each be lowered into the depressions (130) of the multi-well plate. A multilayer titanium electrode (50) according to the invention is in each case formed on the electrode carriers (112). When in use, it forms the electrical counter electrode to the electrode on the bottom of the depression (130) of the multi-well plate.

FIG. 7A shows the amplitude curve (ohmic portion), FIG. 7B shows the phase curve.

EXAMPLE 1

PVD Process for Producing Ti—TiN Electrode Layers

The thermoplastic substrate, on which the titanium electrode is to be created, is placed into a PVD coating chamber, and a vacuum with a pressure of $1\times10^{-6}$ mbar or lower is attained in the chamber via vacuum pumps (booster pump and turbo pump) after approximately 14 to 18 hours.

Coating preparation 1: The chamber is flooded 5 min prior to the beginning of the coating with a flow of 274 sccm of argon, wherein the gas flow is controlled and regulated by means of mass flow controllers.

Coating 1: titanium carrier layer: Coating is started with 500 W RF generator power at 274 sccm of argon flow. When plasma ignites, argon flow is directly regulated down to 100 sccm. The setting of the pure argon flow takes place within a few seconds after the ignition. A 274 sccm flow is only required to facilitate the plasma ignition. The coating duration is 5 to 30 minutes, depending on the thermal capacity of the substrate material. Here, benchmarks are 5 min in the case of polystyrene, 15 min in the case of polyamide, 30 min in the case of stainless steel substrates.

Between the Ti coating and subsequent TiNx coating, the substrates, which are now coated with titanium, are left in the evacuated coating chamber at an argon-gas flow of 100 sccm. They cool down for 1 to 2 hours under these conditions.

Coating preparation 2: 5 min prior to the beginning of the coating, argon flow is increased from 100 sccm to 274 sccm. In addition, a nitrogen flow of 2 sccm is additionally admixed, in order to create the process gas Coating 2: TiNx intermediate layer: The coating is started with 800 W RF generator power at 274 sccm of argon and 2 sccm of N2 flow. When plasma ignites, argon flow is directly regulated down to 180 sccm, in order to create the actual process gas. (The setting of the pure argon flow takes place within a few seconds after the ignition. The 274 sccm flow is only required to facilitate the plasma ignition.)

The coating duration for the titanium-rich TiNx layer is approximately 2 minutes and, in the case of thermally stable substrates (e.g. stainless steel), can be increased to 3 minutes in individual cases.

If a titanium electrode comprising several titanium-rich intermediate layers is to be created, the generator power can be lowered in smaller stages, depending on the desired titanium content for depositing purposes. In the case of each lowering of the generator power, an intermediate layer comprising a lower titanium content than the previous layer is deposited. It may be required to increase the increased argon flow at the beginning of the deposition or to maintain the argon flow increase for the entire duration of the deposition of at least the TiNx intermediate layer.

Coating 3: TiNy cover layer: After 2 or 3 minutes of coating, respectively, with the titanium-rich TiNx layer at 800 W, the generator power is regulated down to 500 W. The process gas mixture remains unchanged (180 sccm of argon and 2 sccm of N2 flow). The sputtering process is not stopped. The deposited titanium-rich TiNx layer can now be coated with a titanium-poorer TiNy layer. The coating duration depends on the desired electrical properties of the electrode (necessary layer thickness) and on the thermal stability of the substrate. Here, guide values are: polystyrene: 5 to 15 min, polyamide: 30 min, stainless steel: 90 min to 150 min. After this time, the generator is turned off in order to stop the coating.

Conclusion of the coating process: After the generator is turned off, the coated substrates remain in the process gas atmosphere, depending on the previous coating time, while the pumps are running The cool-down time corresponds to half the coating time. After this first cool-down phase in the process gas mixture, the nitrogen flow is interrupted, and the argon flow is regulated to 100 sccm. This state, again, is maintained for half the coating time. Following this second cool-down phase, the argon flow is interrupted, the remaining argon is pumped off, and the vacuum pumps are subsequently stopped. After the turbo pump stops, another 5 to 10 min are allowed to pass, before the chamber is opened and the coated substrates are removed.

Figure 1A:
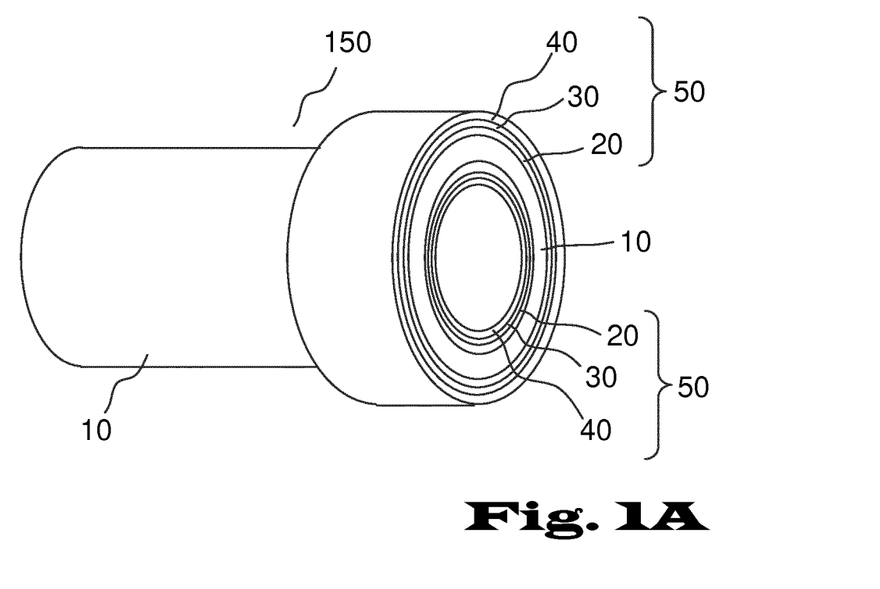
Figure 1B:
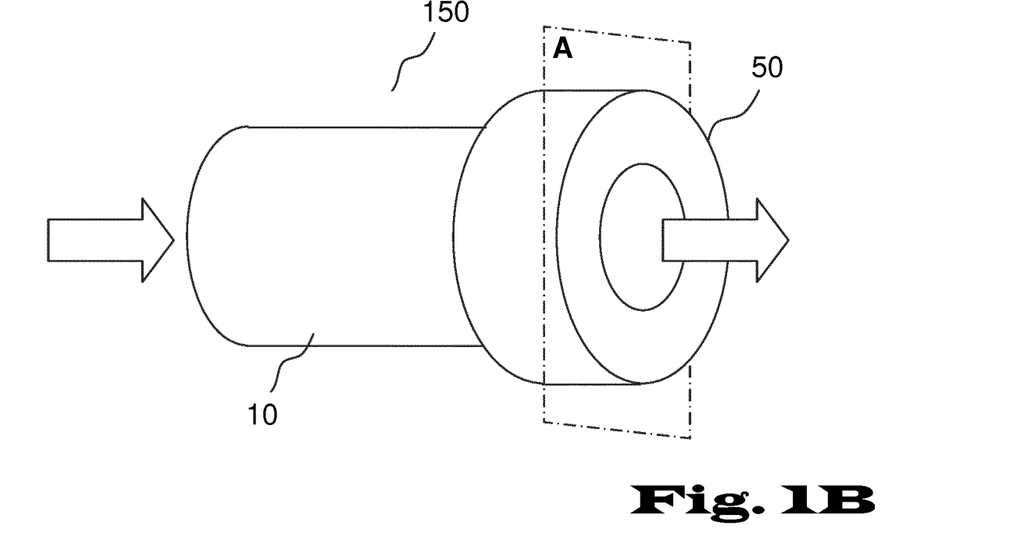
Figure 2:
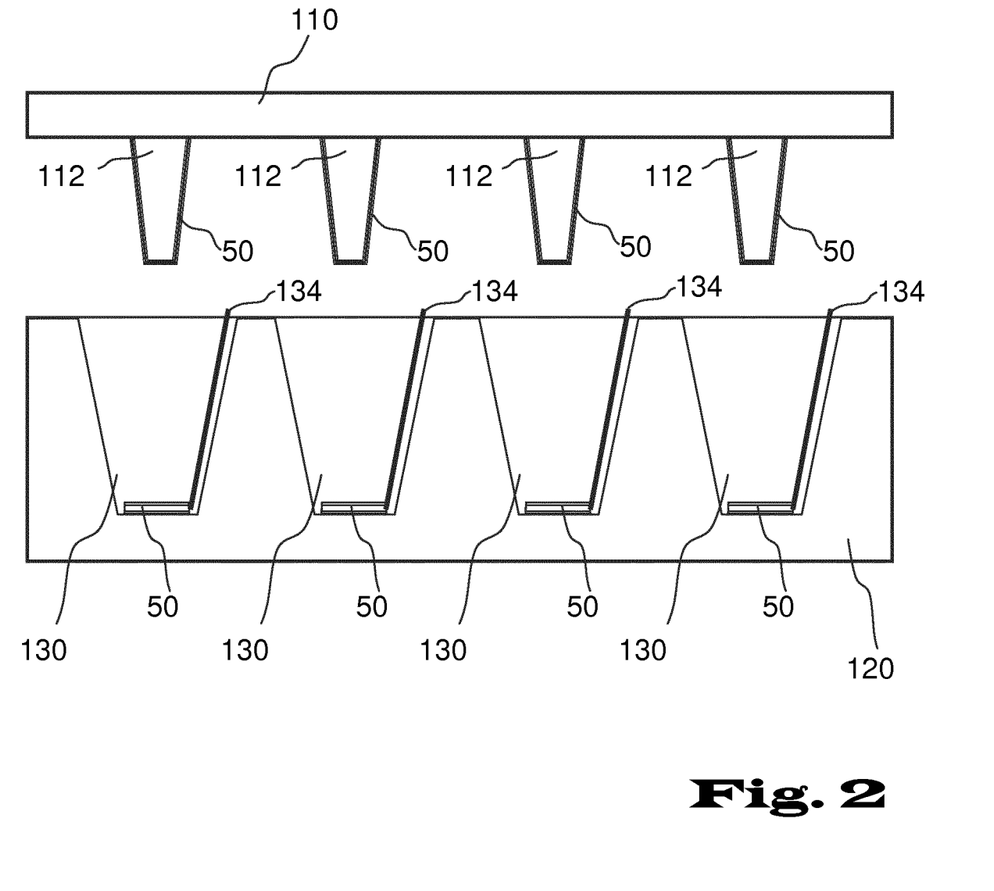
FIG. 2 shows a schematic cross-section through a measuring arrangement according to the invention comprising cell culture plate (multi-well plate) comprising several depressions (wells) (130) arranged next to one another on a common carrier (120). A multilayer titanium electrode (50) according to the invention is formed directly on the bottom of each depression (130). In the illustrated embodiment, an electrical conductor track (134) leads from the electrode (50) at least to the upper edge of the depression (130) and provides for the electrical contacting.
Figure 3:
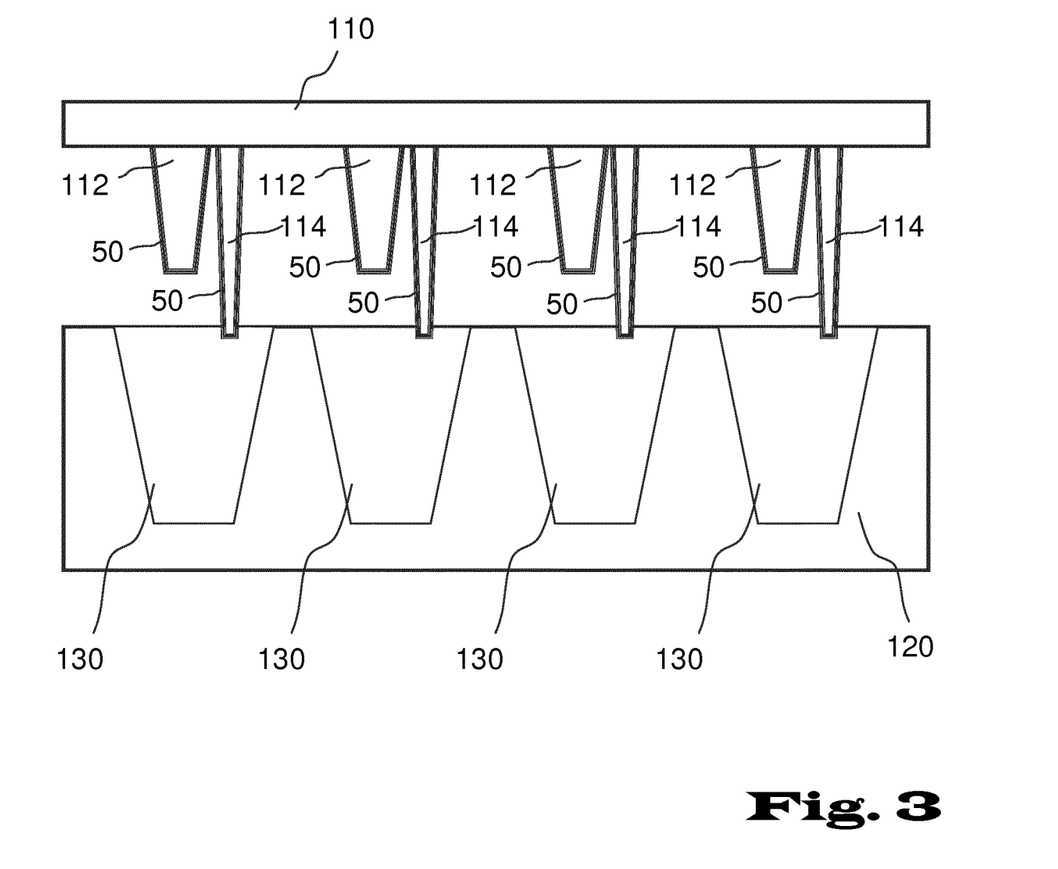
FIG. 3 shows a schematic cross-section through another measuring arrangement according to the invention for use with a conventional cell culture plate (multi-well plate) comprising several depressions (wells) (130) arranged next to one another on a common carrier (120). The measuring arrangement according to the invention is formed as cover or stamp (110). The latter has upper electrode carriers (112) and lower electrode carriers (114), which, when in use, can each be lowered into the depressions (130) of the multi-well plate. A multilayer titanium electrode (50) according to the invention is in each case formed on the electrode carriers (112, 114). When in use, upper electrode carrier (112) and lower electrode carrier (114) serve as electrode and counter electrode in the respective depression (130).
Figure 4:
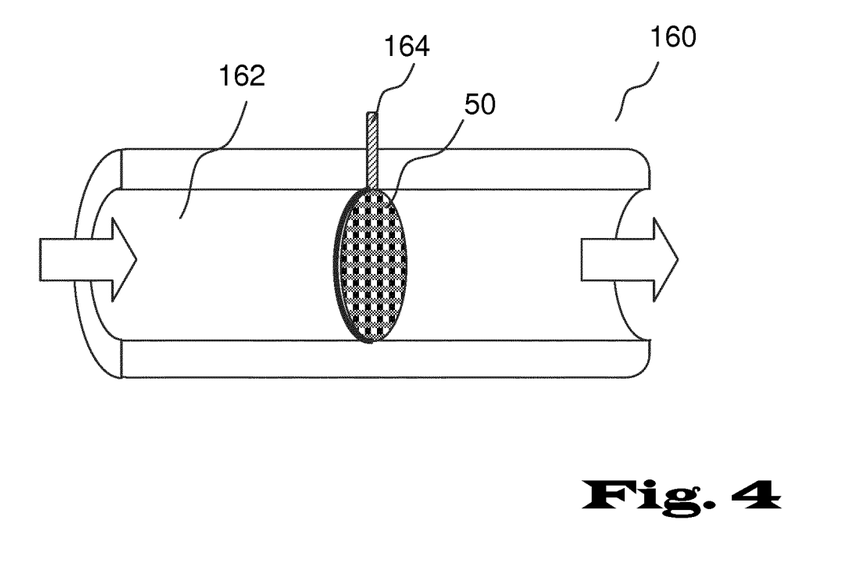
FIG. 4 shows a schematic perspective partially cut view of a measuring module according to the invention in the form of a connecting piece (160) for guiding liquid medium (arrows). The illustration is not scaled. A carrier of polymer, which is in principle net-shaped or grid-shaped, which serves as substrate for the multilayer titanium electrode (50) according to the invention, is used in the media-guiding lumen (162) of the connecting piece (160). A contacting element (164) serves for the electrical connection. The contacting element (164) can be formed by the coated carrier itself.
Figure 5A:
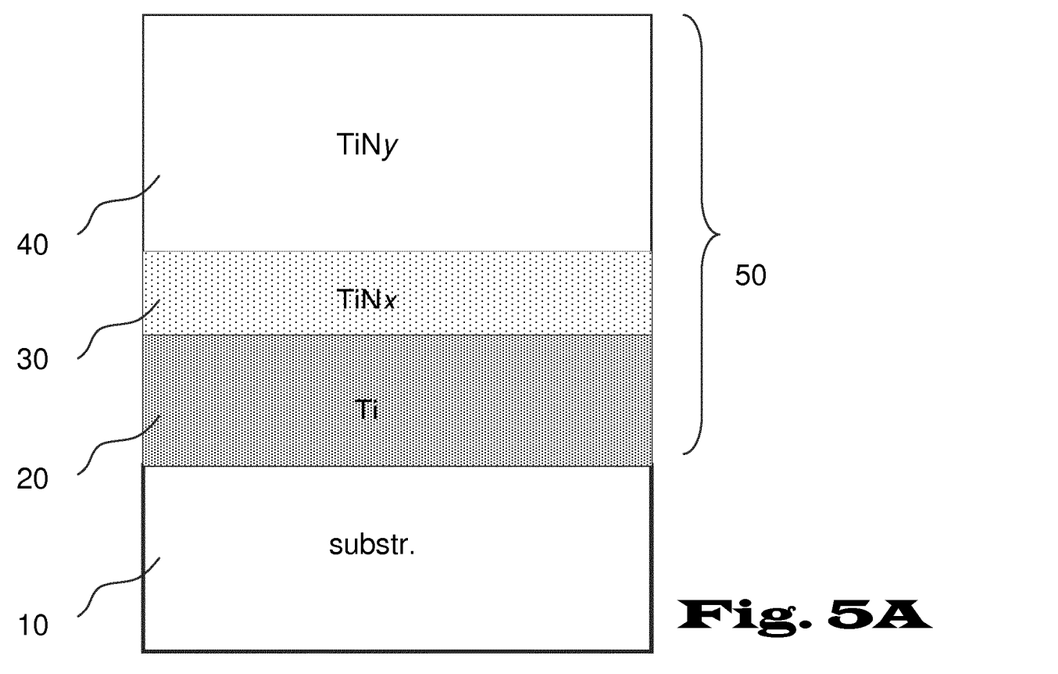
FIG. 5A shows a schematic cross-section through a typical layer sequence of a three-layer titanium electrode (50) according to the invention, which, deposited on a substrate (10), forms the basic configuration of a measuring module according to the invention: A Ti layer (20) is deposited directly on the substrate (10), on it a titanium-rich TiNx intermediate layer (30), on it a titanium-poor TiNy cover layer (40).
Figure 5B:
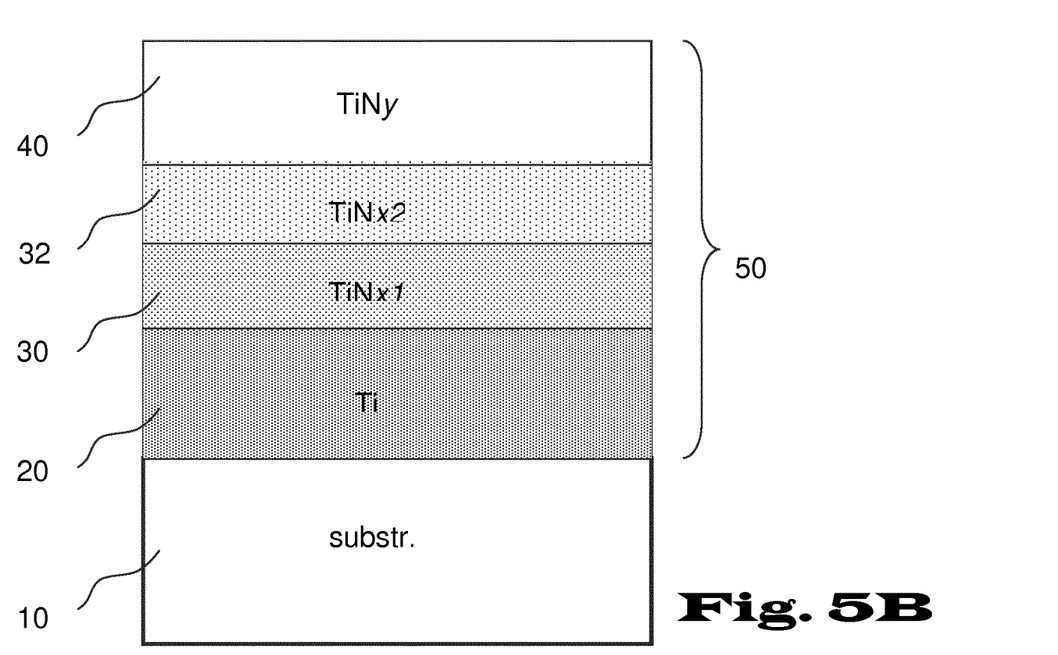
FIG. 5B shows a schematic cross-section through a typical layer sequence of a multilayer titanium electrode (50) according to the invention comprising more than one TiNx intermediate layer: A Ti layer (20) is deposited directly on the substrate (10), on it a first titanium-rich TiNx$_n$ intermediate layer (30), on it at least one further titanium-rich TiNx$_{n+1}$ intermediate layer (32), but which is titanium-poorer than the TiNx$_n$ intermediate layer, on which it is deposited, finally on it a titanium-poor TiNy cover layer (40).
Figure 6:
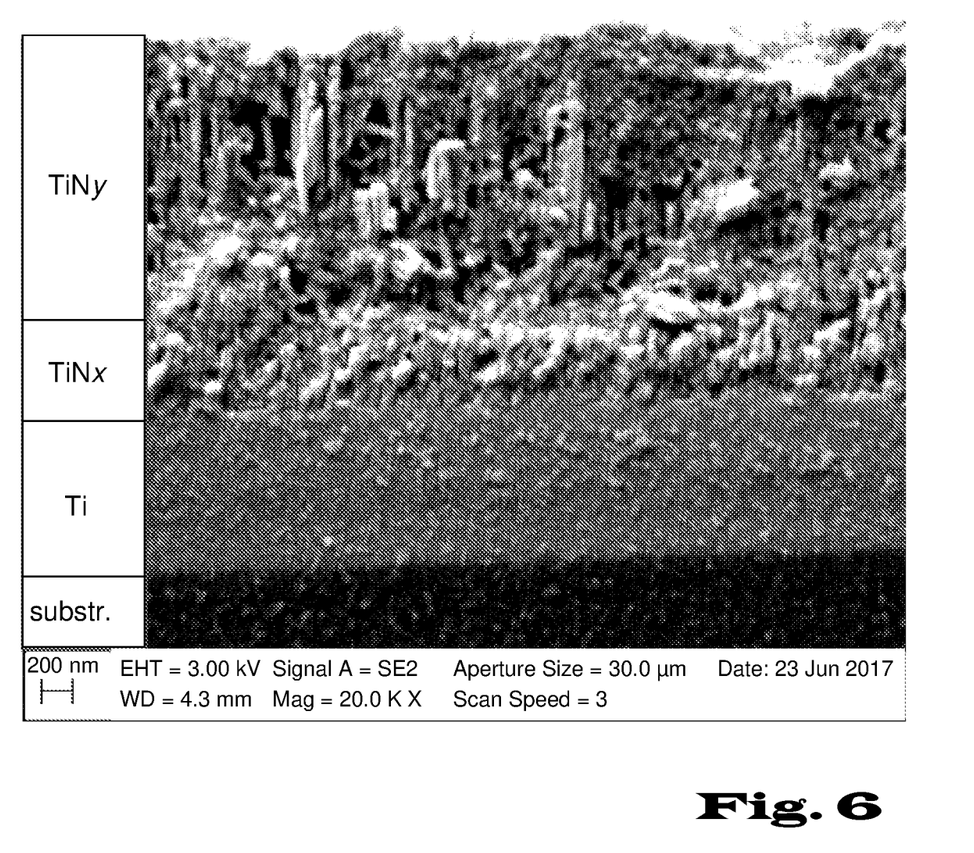
FIG. 6 shows a SEM image of a cross-section through a three-layer titanium electrode (50) according to the invention: a layer of elemental titanium is deposited directly on the substrate, on it a titanium-rich TiNx intermediate layer with a dense structure, on it a titanium-poor TiNy cover layer with open structure.

Results: The SEM picture in FIG. 5 shows the setup of the titanium electrode on the substrate. Depending on the type and temperature compatibility of the substrate, the thickness of the coating can preferably be between 200 and 450 nm. For more temperature-sensitive substrates, a thinner titanium-rich intermediate layer (TiNx) can be deposited, in order to reserve a higher "heat budget" for the following titanium-poorer cover layer (TiNy). For metallic substrates, the titanium-rich intermediate layer (TiNx) can also be designed to be thicker, in particular up to 450 nm.

The TiNx intermediate layer has a higher density than the titanium-poorer TiNy cover layer. This substantiates a good conductivity of the intermediate layer. The more open structure of the titanium-poorer TiNy cover layer substantiates the improved impedance behavior thereof.

EXAMPLE 2

Impedance Behavior of the Titanium Electrode

Very thin titanium electrodes are deposited on polymeric, thermally sensitive carriers (polystyrene). On the one hand, Ti/TiN electrodes with conventional two-layer setup are produced, on the other hand, three-layer titanium electrodes according to the invention of Ti/TiNx/TiNy according to Example 1 are produced. In both cases, the coating parameters are selected such that only very thin layers are created, so as not to damage the thermally sensitive carriers.

Figure 7A:
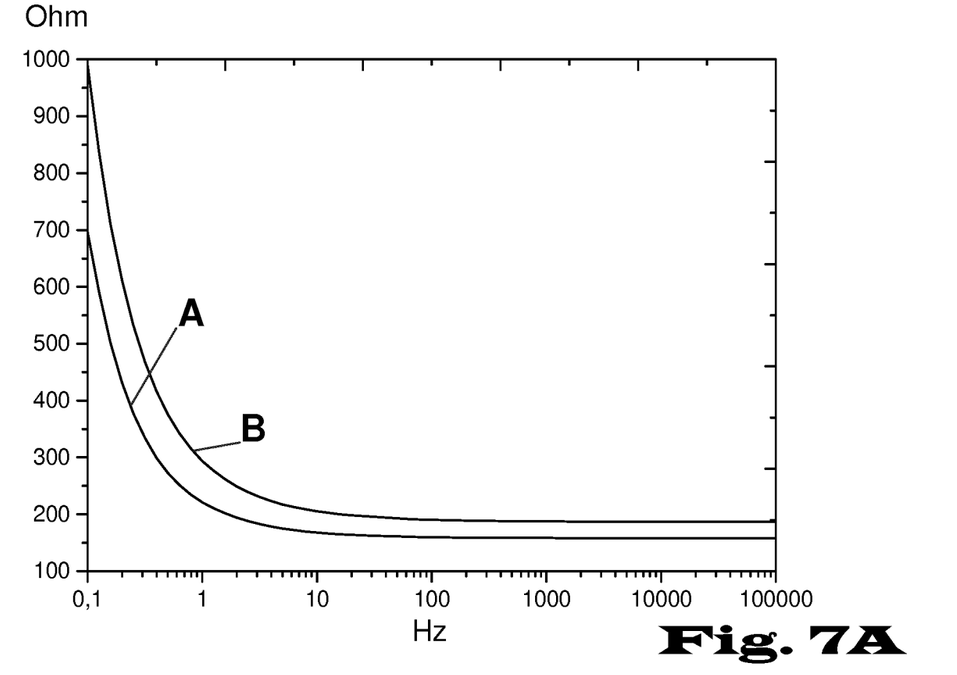
FIGS. 7A and 7B show Bode diagrams of the impedance curve of actual thin titanium electrodes: A=three-layer titanium electrode according to the invention, B=simple Ti/TiN electrode.
Figure 7B:
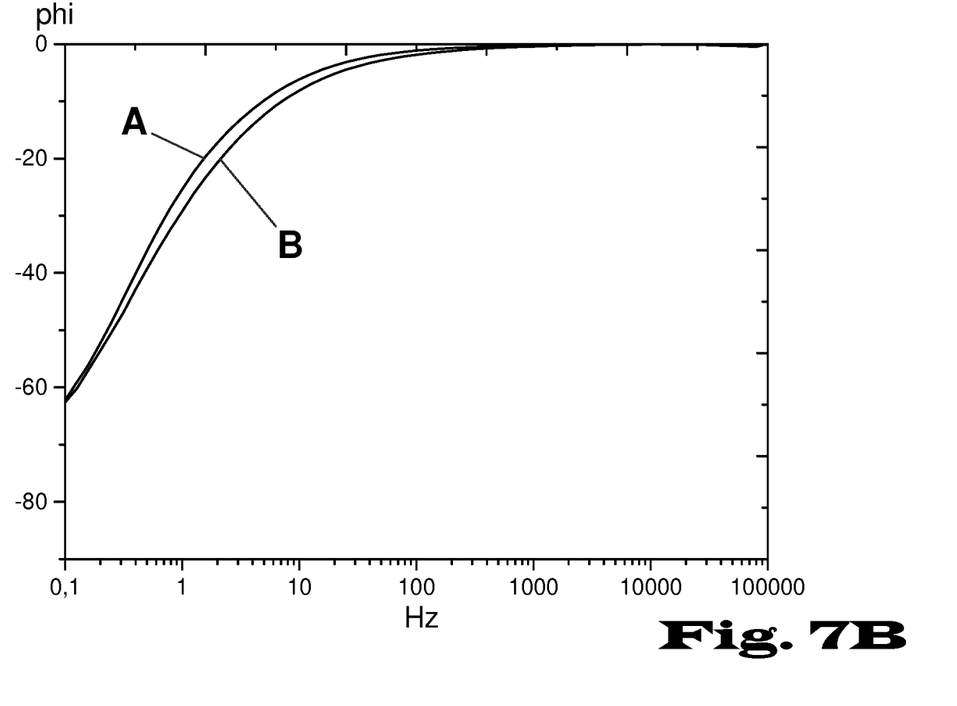
Figure 8:
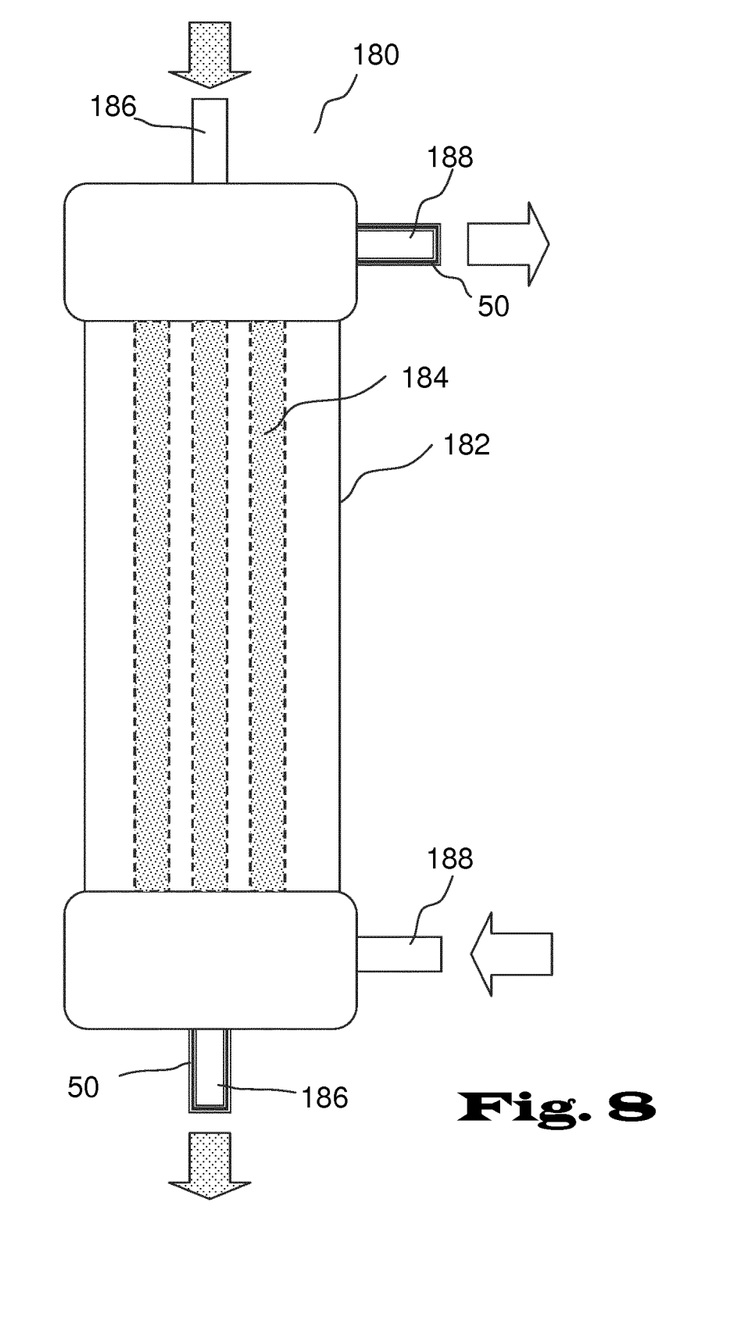
FIG. 8 shows a schematic cross-section through another measuring arrangement according to the invention in the form of a conventional membrane reactor or dialyzer comprising a housing (182) and semi-permeable hollow membranes (184) arranged therein. The interior of the hollow membranes (184) can be perfused via inlets and outlets (186). Separated therefrom, the space surrounding the hollow membranes (184) can be perfused via dialysate inlets and outlets (188). According to the invention, a three-layer titanium electrode (50) is in each case formed at least on an inlet or outlet (186) and at least one dialysate inlet or outlet of the (188), in order to provide for an electrical measurement of the impedance via the hollow membranes (184). A colonization or blockage of the membrane can thus be detected and quantified externally by means of continuous electrical measurements.

In the case of the three-layer titanium electrodes according to the invention, the impedance behavior in resistance (ohmic component) and phase angle (Bode diagram) is significantly improved primarily in the frequency range relevant for the impedance-spectroscopic TEER measurements of biological tissue: the series resistance of the electrode (A) according to the invention is smaller and shows a lower frequency dependence (FIG. 7A), the phase curve is flatter, the phase shift is smaller (FIG. 7B).

The invention claimed is:

1. A titanium electrode (50) apparatus for impedance measurement in aqueous biological media, comprising:
    a substrate (10),
    a Ti carrier layer (20), disposed on the substrate and comprising elemental titanium (Ti),
    one or more titanium-rich titanium nitride ($TiN_x$) intermediate layers (30,32) comprising $TiN_x$, with x smaller than 1 or x equal to 1, disposed on the Ti carrier layer, and
    a titanium-poor titanium nitride ($TiN_y$) cover layer (40), comprising $TiN_y$, with y greater than 1, disposed on the one or more titanium-rich $TiN_x$ intermediate layers.

2. The apparatus according to claim 1, wherein a thickness of the $TiN_y$ cover layer (40) is 0.5 to 10 times, a thickness of the one or more $TiN_x$ intermediate layers (30).

3. The apparatus according to claim 2, wherein the Ti carrier layer, the one or more $TiN_x$ intermediate layers, and the $TiN_y$ cover layer (20, 30, 40) have a thickness ratio of 1-5/1/0.5-10.

4. The apparatus according to claim 1, wherein each of the one or more $TiN_x$ intermediate layers (30,32) has a thickness from 100 to 500 nm.

5. The apparatus according to claim 1, wherein the one or more $TiN_x$ intermediate layers (30,32) consist of TiNX, with x from 0.3 to 1.0.

6. The apparatus according to claim 1, wherein the $TiN_y$ cover layer (40) consists of $TiN_y$, with y from 1.1 to 1.5.

7. The apparatus according to claim 1, wherein the substrate is a polymeric substrate.

8. The apparatus according to claim 7, wherein the polymeric substrate (10) is selected from a group consisting of polystyrene (PS), polyamide (PA), acrylonitrile butadiene styrene (ABS), polylactic acid (PLA), polycarbonate (PC), polyethylene terephthalate (PET), polyethylene (PE), polycaprolactone (PCT), polypropylene (PP), polyetheretherketone (PEEK), polyimide (PI), polyurethane (PU), polyvinylchloride (PVC), and combinations, mixtures, and co-polymers thereof.

9. The apparatus according to claim 7, wherein the apparatus is a cell culture vessel, a multi-well plate, a membrane reactor, a hollow fiber module, or a hose connecting piece.

10. A method for preparing the titanium electrode (50) apparatus according to claim 1 by means of reactive cathode sputtering in a process gas containing argon (Ar) and nitrogen ($N_2$), comprising the steps:
    b) sputtering titanium onto a titanium-covered substrate at generator power, in order to deposit the one or more titanium-rich TiNx intermediate layers, on the titanium-covered substrate,
    c) reducing the generator power, and
    d) sputtering titanium onto the substrate at the reduced generator power in order to deposit the titanium-poor TiNy cover layer on the one or more titanium-rich TiNx intermediate layer formed in step b).

11. The method according to claim 10, wherein the steps b) and c) are passed through several times, in order to deposit at least one further titanium nitride intermediate layer (32), comprising the titanium-rich TiNx, on a first titanium nitride intermediate layer (30), wherein in steps c) for each pass-through the generator power is in each case reduced as compared to the previous pass-through, in order to form a titanium-poorer further titanium nitride intermediate layer (32) on one of the respective titanium-richer titanium nitride intermediate layer (30), which had in each case been deposited beforehand.

12. The method according to claim 10, wherein the generator power in step b) is 1.2 to 2.4 times the reduced generator power in step d).

13. The method according to claim 10, wherein the composition of the process gas (Ar/$N_2$), based on the $N_2$ partial pressure, is held constant while performing steps b) to d).

14. The method according to claim 10, further comprising a step preceding step b):
    a) depositing a titanium layer (20) on an electrode substrate (10) to form the titanium-covered substrate.

* * * * *